United States Patent
Campbell et al.

(10) Patent No.: US 7,510,723 B2
(45) Date of Patent: Mar. 31, 2009

(54) PESTICIDES BASED ON VICINAL DIOLS

(75) Inventors: John Campbell, Zionsville, IN (US); Andrew Carver, West Lothian (GB)

(73) Assignee: Ectopharma Limited, Edinburgh (GB)

( * ) Notice: Subject to any disclaimer, the term of this patent is extended or adjusted under 35 U.S.C. 154(b) by 732 days.

(21) Appl. No.: 10/468,834

(22) PCT Filed: Feb. 28, 2002

(86) PCT No.: PCT/GB02/00825

§ 371 (c)(1), (2), (4) Date: Dec. 2, 2003

(87) PCT Pub. No.: WO02/069707

PCT Pub. Date: Sep. 12, 2002

(65) Prior Publication Data

US 2004/0091512 A1 May 13, 2004

(30) Foreign Application Priority Data

Mar. 2, 2001 (GB) ................................ 0105229.9

(51) Int. Cl.
*A01N 25/32* (2006.01)
(52) U.S. Cl. ........................ 424/406; 424/405; 514/738
(58) Field of Classification Search .................. None
See application file for complete search history.

(56) References Cited

U.S. PATENT DOCUMENTS

| | | | |
|---|---|---|---|
| 2,212,701 A | 8/1940 | Reynolds | |
| 2,356,801 A | 8/1944 | Travis et al. | |
| 2,407,205 A | 9/1946 | Wilkes | |
| 2,946,716 A | 7/1960 | Hessel | |
| 4,049,830 A | 9/1977 | Pugliese | |
| 4,147,800 A | 4/1979 | Singer et al. | |
| 4,160,033 A | 7/1979 | Garrett et al. | |
| 4,226,881 A | 10/1980 | Barer | |
| 4,291,497 A | 9/1981 | Manankov | |
| 4,332,817 A | 6/1982 | Barer | |
| 4,368,207 A | 1/1983 | Lover et al. | |
| 5,130,136 A | 7/1992 | Shono et al. | |
| 5,166,193 A | 11/1992 | Levin et al. | |
| 5,190,978 A | 3/1993 | Nakamura et al. | |
| 5,288,483 A | 2/1994 | Cardin et al. | |
| 5,342,630 A | 8/1994 | Jones | |
| 5,587,401 A | 12/1996 | Vander Meer et al. | |
| 5,648,390 A | 7/1997 | Vander Meer et al. | |

(Continued)

FOREIGN PATENT DOCUMENTS

DE 2204943 8/1973

(Continued)

OTHER PUBLICATIONS

XP-002206755, Database WPI, Derwent Publications Ltd., London, Aug. 10, 1976.

*Primary Examiner*—Neil Levy
(74) *Attorney, Agent, or Firm*—Jacobson Holman PLLC

(57) ABSTRACT

Pesticides based on vicinal diols, are available to control arthropod ectoparasites such as *Pediculus Humanus*, *Dermatophagoides pteronyssinus*, *Musca domestica*, the Blattidae, *Blatella Germanica*, and *Periplaneta Americana*, by introducing to the locus of an infestation of the pest, a composition containing as active ingredient a vicinal diol.

11 Claims, 1 Drawing Sheet

U.S. PATENT DOCUMENTS

| | | |
|---|---|---|
| 5,721,274 A | 2/1998 | Vander Meer et al. |
| 5,739,172 A | 4/1998 | Jones |
| 5,910,323 A | 6/1999 | Lajoie et al. |
| 5,925,371 A | 7/1999 | Ishiwatari |
| 5,928,634 A | 7/1999 | Uick et al. |
| 6,071,973 A | 6/2000 | Vander Meer et al. |
| 6,074,634 A | 6/2000 | Lopez, Jr. et al. |
| 6,077,521 A | 6/2000 | Hammond et al. |
| 6,123,953 A * | 9/2000 | Greff .................. 424/407 |
| 6,147,091 A | 11/2000 | Krüger et al. |
| 6,183,766 B1 | 2/2001 | Sine et al. |
| 6,245,328 B1 | 6/2001 | Fettkoetter et al. |
| 6,294,577 B1 | 9/2001 | Vander Meer et al. |
| 6,395,776 B1 | 5/2002 | Losel et al. |

FOREIGN PATENT DOCUMENTS

| | | |
|---|---|---|
| DE | 251488 | 11/1987 |
| DE | 19841794 | 3/2000 |
| EP | 0935960 | 8/1999 |
| EP | 0985408 | 3/2000 |
| EP | 985408 | 3/2000 |
| GB | 463544 | 3/1937 |
| GB | 687850 | 2/1953 |
| GB | 1214970 | 12/1970 |
| GB | 1604856 | 12/1981 |
| GB | 1604859 | 12/1981 |
| GB | 2322300 | 8/1998 |
| JP | 57158709 | 9/1982 |
| JP | 58157702 | 9/1983 |
| JP | 59222402 | 12/1984 |
| JP | 9002841 | 1/1997 |
| WO | WO 8912673 | 12/1989 |
| WO | WO 9116032 | 10/1991 |
| WO | WO 9205699 | 4/1992 |
| WO | WO 9424862 | 11/1994 |
| WO | WO 9601832 | 1/1996 |
| WO | WO 9633800 | 10/1996 |
| WO | WO 9963818 | 12/1999 |

* cited by examiner

PESTICIDES BASED ON VICINAL DIOLS

This is a nationalization of PCT/GB02/00825 filed Feb. 28, 2002 and published in English.

This invention relates to the use of hydroxy-substituted hydrocarbyl compounds, particularly vicinal diols such as 1,2-alkyldiols to control arthropod pests.

BACKGROUND TO THE INVENTION

There is a need for a class of pesticidal agents that is able to kill a wide range of common arthropod pests of humans, their companion animals and livestock, notably those belonging to the phyletic classes Arachnida (ticks and mites) and Insecta (cockroaches, fleas, flies, silverfish, lice). Given the intimate nature of the association of these parasites with their human or animal hosts, such agents must, for any practical purpose, be relatively non-toxic to the host. There is a further need for a class of pesticidal agents that is able to kill a wide range of arthropod pests on foliage, in the agriculture and garden sectors.

It is also advantageous that the pesticide in either case is ecologically-friendly (i.e. biodegradable).

A large number of chemical compounds have been developed and marketed as pesticidal agents. However, few satisfy the triple criteria (1) generalised toxicity to arthropod pests; (2) comparatively low toxicity to human and animal hosts and (3) good biodegradability.

OBJECTS OF THE INVENTION

An object of the present invention is to provide alternative pesticidal agents that will obviate or mitigate at least some of the drawbacks of currently commercially available products. In particular it is an object to provide a method of control of arthropod.

SUMMARY OF THE INVENTION

Now it is discovered that vicinal diols satisfy the desired criteria very well. In particular, the current research has revealed that certain compounds of the class of vicinal diols which have the chemical formula, $R(OH)_2$, wherein the hydroxyl groups occupy vicinal positions and R is a hydrocarbyl chain that is optionally derivatised or substituted, offer remarkably good efficacy as pesticides of the desired qualities. The limiting number of carbons in the R group is a matter of ongoing research. However, good results are observed where the compound has at least one hydrocarbyl chain of length n+2 atoms, wherein the value of n is preferably at least 2 carbons, and the vicinal hydroxyls occupy a terminal position, preferably having hydroxyls at 1,2-positions such that the diol forms a head group with a lipophilic tail. Differing activities are observed with changes in n value. This leads to preferences amongst them and differences in activity for lower alkyl groups in comparison with higher alkyl groups ($C_6$ and above). Thus n may have a value of up to 20, but compounds wherein n has a value of from 2 to 12 inclusive are of particular interest currently. Such diols are chiral in nature with, for example, the second carbon being a chiral centre in the case of 1,2 diols. A racemic mixture is usefully employed in the present invention but single optical isomers (enantiomers), or mixtures containing a preponderance of one or more particular optical isomer(s) can also serve the purposes of the invention. For example both enantiomers of 1,2-decanediol have been shown to be effective against lice in comparable fashion to the racemic mixture whose results are tabulated hereinafter.

The use of 1,2-alkyldiols for the control of bacterial infection has already been shown. Kazunori (Japanese patent application No. JP 50-15 925/Publication No. 51-91 327) teaches that 1,2-alkyl diols, especially medium-chain homologues (n=5–9), are efficient bacteria- and fungi-static agents with general application. Similarly Pugliese (U.S. Pat. No. 4,049,830) teaches the application of 1,2-alkyl diols for the sterilisation of bovine teats as a prophylactic treatment for bacterial bovine mastitis. Similarly Greff (U.S. Pat. No. 6,123,953) teaches the use of 1,2-diols for generalised topical application in the control of bacteria that cause skin ailments including mastitis, acne and dandruff. Similarly Agostini and Cupferman (European patent application EP 0 935 960 A1) teach cosmetic formulations containing an 1,2-alkyl diol as an antibacterial agent.

Airs in GB 687 850 has taught the use of certain vicinal diols as insect repellents together with known non-solvent insecticides. The potential for the application of vicinal diols as the active ingredient in the control of pests by killing them or their ova has not heretofore been considered. Lover and Singer et al (U.S. Pat. No. 4,368,207) teach the use of a range of monohydric alcohols against lice, their ova, and mites. Similarly Lover and Singer et al teach the use of non-vicinal, particularly 1,3 diols, in United Kingdom patent UK 1 604 856. That patent suggests such compounds for the control of ectoparasites and their ova.

It has now been discovered that vicinal diols, in a preferred embodiment the readily available 1,2 diols, have surprisingly enhanced pesticidal properties in comparison with mono-ols or non-vicinal diols. 1,2-Alkyldiols may be used to kill a wide range of common arthropod pests, notably arachnids, such as ticks and mites, and insects, such as flies, cockroaches, silverfish and lice, and ovicidal effects can be demonstrated. Moreover these are found to be biodegradable, and eminently suitable as valuable pesticides for a wide variety of uses and applications.

Whilst the potency and efficacy of the vicinal diols per se is proven, so that the selected diols themselves are directly useful, in most cases the target pests can be effectively combated with diluted amounts thereof, and for some purposes preferred delivery forms will offer additional technical advantages.

Accordingly, further according to the invention there are provided formulations that are suitable for contact application of such vicinal diols or their derivatives, comprising at least one such vicinal diol in a physiologically tolerable carrier, for the control of specific pest-induced ailments of humans and animals, including head- or body-louse infection, carpet mite infestation, sheep-scab mite infection and blow-fly strike.

Typically the formulations will comprise compositions of the preferred vicinal diols alone or in combination, together with suitable auxiliaries as required, with a carrier adapted to deliver an effective amount of the vicinal diol(s) to the locus of a pest infestation. The carrier will usually be selected with a view to prolonging contact with the target pest. Depending upon the infestation targeted, the carrier may be a finely divided solid or a liquid, and may be selected from powder, resins, and aqueous or organic fluids. Therefore, a suitable formulating aid may be selected from liquid vehicles, solid carriers, auxiliaries, emulsifiers, dispersants, resins, gums, adherents, diluents and extenders.

The pesticidal composition may be suitably prepared for delivery in a formulation selected from a solution, a dispersion, an emulsion, a dusting powder, a paste, an aerosol, a cream, a foam, a coated substrate e.g. tacky paper, a pellet or block e.g. as in a bait for a trap. The skilled worker will observe the need to select a physiologically benign or tolerable carrier when the pest is to be combated directly upon a live host, and may select such carriers from pharmaceutically acceptable carriers, especially those intended for topical application, to form creams, gels, pastes and ointments, aerated (foam/mousse) compositions or dusting powders e.g. talc.

BRIEF DESCRIPTION OF THE DRAWINGS

The invention will now be described in more detail by way of example with reference where appropriate to the accompanying drawings in which.

Figure 1:
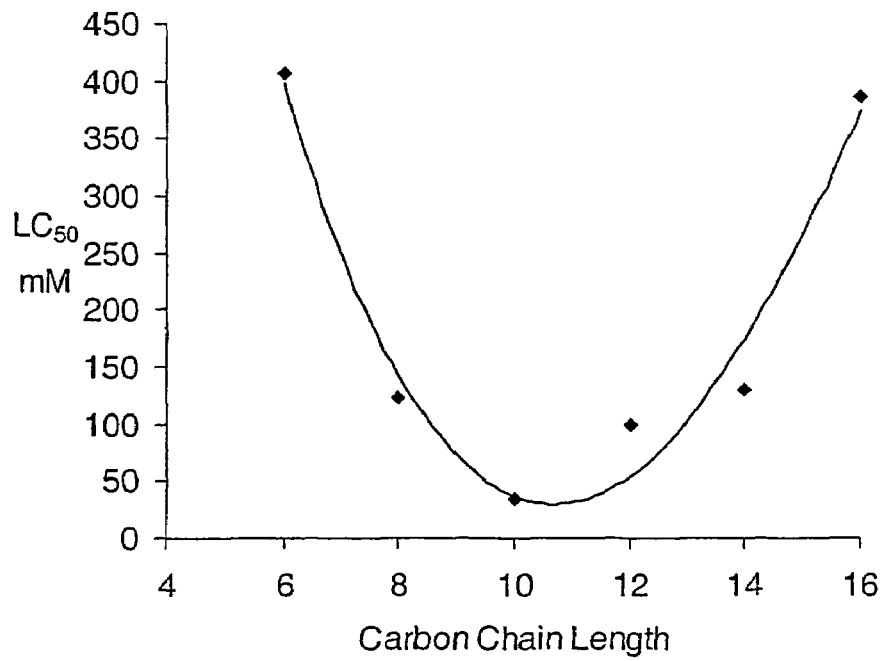
FIG. 1 is a graph of $LC_{50}$ values found for a range of 1,2 diols against the human body louse (*Pediculus humanus*)

The following results will serve to illustrate the utility of selected vicinal diols against a range of pests but should not be considered to prescribe limits to their effectiveness against these or other organisms. Demonstration of efficacy of the selected vicinal diols herein is not intended to exclude analogues thereof except as may be specifically stated herein and attention is directed to the claims hereinafter which define the scope of the invention.

EXAMPLE 1

Efficacy Contra *Pediculus humanus*

The pesticidal efficacy of compositions provided by this invention is demonstrated firstly with regard to the human body louse (*Pediculus humanus*), using vicinal diols in tests according to accepted industry protocols.

The special value and unique nature of vicinal diols is illustrated in Tables 1 and 2 wherein the $LC_{50}$ values, measured in tests against lice, for a range of diols and mono-ols are tabulated. Table 1 shows the surprising potency of the vicinal diols in comparison to 1,3 and other non-vicinal diols. For example 1,2-decanediol is significantly superior to 1,3-decanediol and the benefit of the vicinal compounds is apparent in the Table for all the examples of chain length shown.

Table 2 shows similar superiority of the vicinal diols over mono-ols and some triols. The best mono-ol tested has only 36% of the potency found for 1,2-decanediol. The superior potency of the vicinal diols provides the benefit that they can provide effective control of a pest even when applied in a less than ideal manner to the target organisms. A yet further benefit of these compounds is that they have been shown to be readily metabolised by common soil bacteria, derived from several different locations, and so will biodegrade readily when dispersed in the environment.

TABLE 1

| Compound | Diol Type | $LC_{50}$ value (mMol) | Potency index* (%) |
| --- | --- | --- | --- |
| 1,2-Butanediol | Vicinal | >700 | Not effective |
| 1,3-Butanediol | Non-vicinal | >2000 | Not effective |
| 1,2-Hexanediol | Vicinal | >200 | 6 |
| 1,5-Hexanediol | Non-vicinal | Not calculable | Not effective |
| 1,6-Hexanediol | Non-vicinal | Not calculable | Not effective |
| 2,5-Hexanediol | Non-vicinal | Not calculable | Not effective |
| 1,2-Octanediol | Vicinal | 40 | 30 |
| 1,3-Octanediol | Non-vicinal | >400 | Not effective |
| 1,2-Decanediol | Vicinal | 12 | 100 |
| 1,3-Decanediol | Non-vicinal | 40 | 30 |

*The potency index compares the $LC_{50}$ value found with that of 1,2-decanediol (=100%)

TABLE 2

| Compound | $LC_{50}$ value (mMol) | *Potency Index (%) |
| --- | --- | --- |
| 1,2,3-Hexanetriol | Not calculable | Not effective |
| 1,2,6-Hexanetriol | Not calculable | Not effective |
| 2-Ethyl-1-hexanol | 300 | 4 |
| 2-Ethyl-1,3-hexanediol | 60 | 20 |
| 1-Decanol | 35 | 32 |
| 2-Decanol | 37 | 34 |
| 4-Decanol | 183 | 6 |
| 9-Decene-1-ol | 33 | 36 |
| 1,2-Decanediol | 12 | 100 |
| 3-Ethyl-1-decanol | 62 | 20 |
| 3-Octyl-1,2-decanediol | 97 | 12 |
| 3-Ethyl-1,2-decanediol | Not calculable | Not effective |

*The potency index compares the $LC_{50}$ value found with that of 1,2-decanediol (=100%).

The effect of diol chain length on activity is illustrated in FIG. 1, by way of a graph of the $LC_{50}$ values found for a range of 1,2 diols against the human body louse.

These results show that 1,2 diols have pediculicidal activity, to the extent that $C_4$ to $C_{16}$ diols are active, and those from $C_8$ to $C_{14}$ are preferred, with the most preferred being 1,2-octanediol, 1,2-decanediol and 1,2-dodecanediol.

Figure 2:
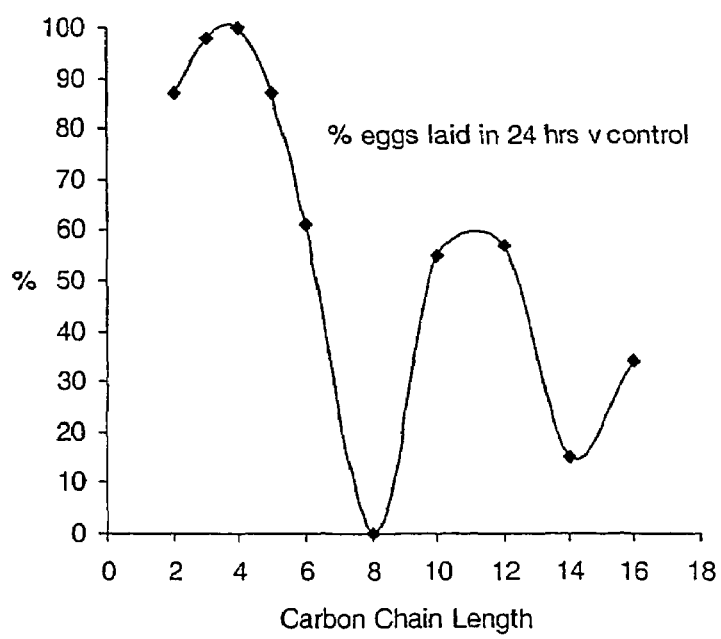
FIG. 2 is a further graph illustrating a relationship between diol chain length and egg-laying activity of treated lice.

FIG. 2 demonstrates a further a beneficial property of the subject matter of the invention, namely the inhibition of egg laying, an important feature in that the life cycle of the target organism is interrupted when egg laying is inhibited or stopped. This is observed by considering the graphic illustration of efficacy of a range of diols which shows that as diol chain length increases egg laying activity of treated lice declines substantially. 1,2-Octanediol is especially efficacious in the prevention of egg laying.

Ovicidal activity has been observed but research on this aspect of activity is continuing and the data is not included in this submission.

EXAMPLE 2

Efficacy Contra *Dermatophagoides pteronyssinus*

The utility of the vicinal diols is further illustrated by the results of experiments against the house dust mite *Dermatophagoides pteronyssinus* according to accepted industry protocols. Mites were sealed in a cotton envelope and briefly immersed (5 seconds) in dilute solutions (2.5%) of selected diols. The mites were examined one hour after immersion and mortality calculated. The results are shown in Table 3 below with comparative results for a proprietary carpet shampoo, permethrin insecticide and water (as controls).

TABLE 3

| Treatment | Mortality (%) |
|---|---|
| 1,2-Octanediol | 65 |
| 1,2-Decanediol | 95 |
| Water | 3 |
| 3% carpet shampoo | 3 |
| 0.25% Permethrin | 100 |

EXAMPLE 3

Efficacy Contra *Musca domestica*

A further example of the use of the compounds of the present invention is shown by testing decane-1,2-diol against house flies in a standard industry protocol for insecticides. More than 80% mortality was observed after 24 hours contrasting with decane-1,10-diol which did not exhibit insecticidal activity.

EXAMPLE 4

Formulation and Application

Vicinal diols are readily formulated in aqueous systems using non-toxic co-solvents such as isopropyl alcohol or by use of surfactants such as Tween®. This makes them eminently suitable for inclusion into many household or industrial, pesticidal or cleansing products. In particular they can be incorporated into pharmaceutical preparations for use on humans or animals. The treatment of lice and cockroaches with formulations containing 1,2-octanediol or 1,2-decanediol is tabulated in Table 4 along with control results for the solvent systems employed. In a procedure following standard industry protocols the subject animals were immersed for a few seconds in the test formulations and blotted dry. Mortality after 24 hrs was measured for the lice, after 1 hr for the cockroaches.

TABLE 4

| Treatment | Lice mortality after 24 hr (%) | Cockroach mortality after 1 hr (%) |
|---|---|---|
| 1,2-Octanediol in 1.5% Tween20 ® | 100 | 100 |
| 1,2-Octanediol in 50% isopropyl alcohol | 100 | 100 |
| 1,2-Decanediol in 7% Tween20 ® | 100 | 100 |
| 1,2-Decanediol in 50% isopropyl alcohol | 100 | 100 |
| 0.25% Permethrin in Water | 100 | 100 |
| Water | 4 | 0 |
| 50% isopropyl alcohol | 4 | 0 |
| 1.5% Tween20 ® | 0 | 0 |
| 7% Tween20 ® | 13 | 0 |

INDUSTRIAL APPLICABILITY

In view of the aforesaid advantages and pesticidal properties of the compounds used in the compositions described herein, the invention will be usefully applied in dealing with pests encountered in agriculture, horticulture, human health, hygiene and veterinary medicine.

The invention claimed is:

1. A method of treating an infestation of lice by killing the lice or rendering the lice moribund, comprising (1) locating a lice infestation or their ova, and (2) applying to the lice infestation or their ova an effective amount of at least one vicinal diol R(OH)$_2$, wherein the vicinal diol is selected from the group consisting of unbranched, unsubstituted aliphatic 1,2-vicinol diols having an aliphatic chain comprising 8-14 carbon atoms.

2. The method of claim 1, wherein the lice infestation comprises a head louse infestation.

3. The method of claim 1, wherein the lice infestation comprises a body louse infestation.

4. The method of claim 1, wherein the arthropod infestation comprises an infestation of *Pediculus humanus*.

5. The method of claim 1, wherein the vicinal diol is selected from the group consisting of unsubstituted aliphatic 1,2-vicinol diols having an aliphatic chain comprising 8-12 carbon atoms.

6. The method of claim 5, wherein the vicinal diol comprises 1,2-octanediol.

7. The method of claim 5, wherein the vicinal diol comprises 1,2-decanediol.

8. The method of claim 5, wherein the vicinal diol comprises 1,2-dodecanediol.

9. The method of claim 1, wherein the vicinal diol is applied as a composition consisting essentially of the vicinal diol and at least one physiologically tolerable carrier.

10. The method of claim 6, wherein the vicinal diol is applied as a composition consisting essentially of the vicinal diol and at least one physiologically tolerable carrier.

11. The method of claim 5, wherein the arthropod infestation comprises an infestation of *Pediculus humanus*.

* * * * *